United States Patent [19]
Luloh

[11] Patent Number: 5,793,524
[45] Date of Patent: Aug. 11, 1998

[54] DEVICE FOR NON-CONTACT WIDE-ANGLE VIEWING OF FUNDUS DURING VITRECTOMY

[76] Inventor: K. Peter Luloh, 343 Vista Oak Dr., Longwood, Fla. 32779

[21] Appl. No.: 905,412

[22] Filed: Aug. 4, 1997

[51] Int. Cl.[6] .................................................. G02B 21/00
[52] U.S. Cl. ........................... 359/381; 359/368; 359/380
[58] Field of Search ..................... 359/362–363, 359/368–390, 656–661, 808–830; 351/216–219, 229–236, 245, 247, 178; 600/101, 102, 166, 172; 604/51, 175, 178, 239

[56] References Cited

U.S. PATENT DOCUMENTS

| | | | |
|---|---|---|---|
| 4,690,522 | 9/1987 | Welsh | 359/390 |
| 4,807,989 | 2/1989 | Nagano et al. | 351/206 |
| 4,856,872 | 8/1989 | Spitznas et al. | 359/826 |
| 5,009,487 | 4/1991 | Reiner | 359/376 |
| 5,282,085 | 1/1994 | Volkert et al. | 359/377 |
| 5,425,730 | 6/1995 | Luloh | 606/15 |
| 5,526,074 | 6/1996 | Volk | 351/219 |
| 5,588,949 | 12/1996 | Taylor et al. | 600/166 |

*Primary Examiner*—Thong Nguyen
*Attorney, Agent, or Firm*—James H. Beusse; Maguire, Voorhis & Wells

[57] ABSTRACT

A wide-angle viewing attachment for an ocular microscope includes a first lens attached to the microscope and a second lens independently mountable with respect to the microscope. The second lens is positionable proximal to an eye of a surgical patient and is maintained in the proximal position by an attachment system including a support member coupled in a fixed position to an operating table on which the patient is reclined. A first support rod extends vertically from the support member and a clamp member is adjustably mounted on the support rod. A horizontally extending second support rod is adjustably coupled to the clamp member and terminates at one end in a generally flat plate. A lens carrier includes a spring clamp for holding the second lens and a support arm extending generally horizontally with respect to the first support rod. The carrier terminates in a magnet assembly which holds the lens carrier to the flat plate.

7 Claims, 2 Drawing Sheets

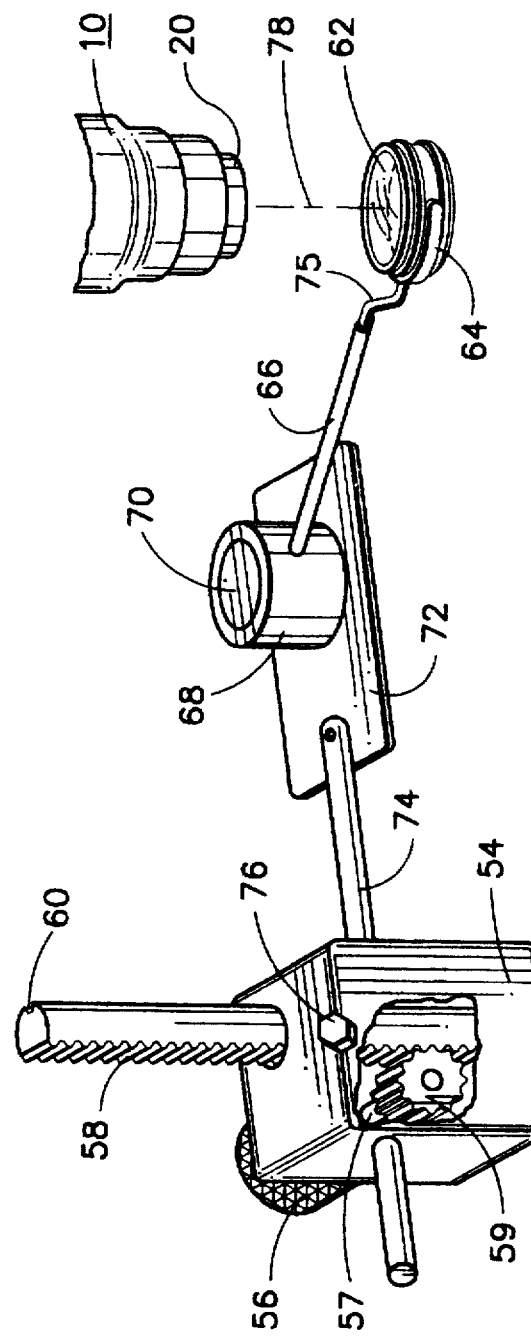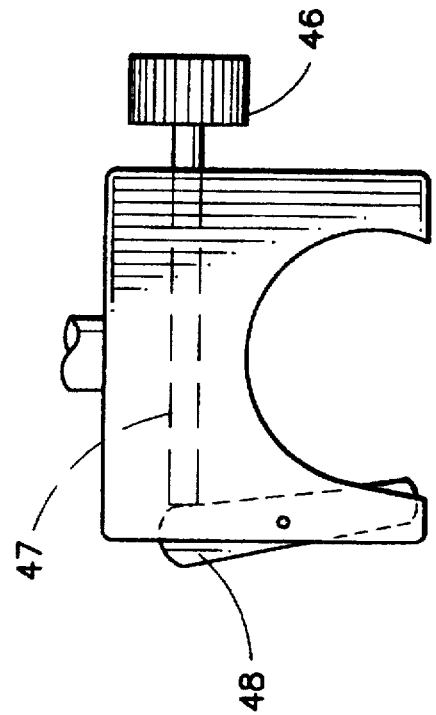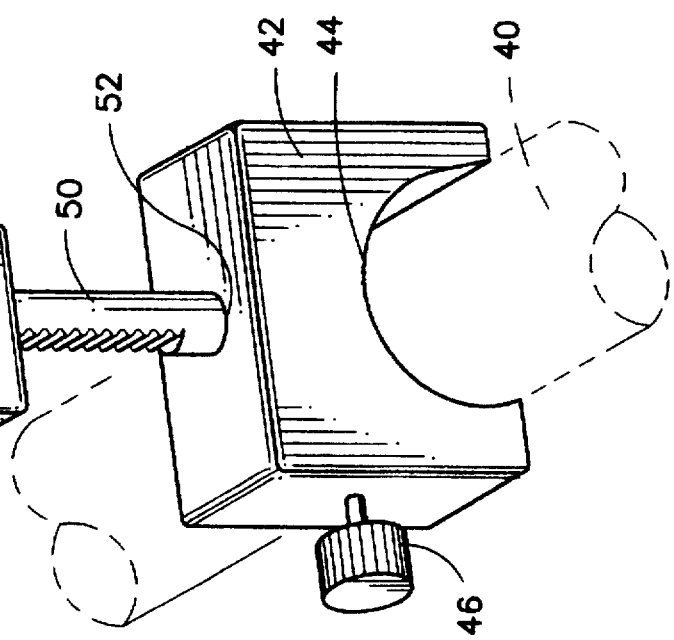
FIG. 2
FIG. 3

DEVICE FOR NON-CONTACT WIDE-ANGLE VIEWING OF FUNDUS DURING VITRECTOMY

FIELD OF THE INVENTION

The invention relates to an attachment for use with microscopes, in particular for stereomicroscopes for facilitating a contact-free viewing of a freely movable eye of a patient, in particular the fundus of the eye.

BACKGROUND OF THE INVENTION

It is known to place a contact lens onto the eye to view the fundus of the eye. The contact lens makes it possible to view image sections of up to 20° on the fundus. Furthermore, a so-called "Panfunduscope" is known, which enables a view of up to 150° of the fundus. However, a disadvantage of this known panfunduscope is that it requires a placement directly onto the eye. This makes complicated resetting operations necessary during surgeries, which must be carried out both in front of the eye lens and also behind the eye lens, so that both surgeries can be carried out with one surgery stereomicroscope. When using only one contact lens, this is avoided. However, the obtained 20° image section is relatively small, so that the microscope must often be reset, which is also disadvantageous during such surgeries.

U.S. Pat. No. 4,856,872 discloses an attachment for microscopes, in particular for stereomicroscopes for facilitating a contact-free viewing of the fundus, which is attached to the microscope or to the stereomicroscope. The attachment of the '872 patent consists of two lenses, the distance between which can be adjusted for the purpose of compensating for the sight deficiency of an eye of the patient and which can be connected to the stereomicroscope through a screw or bayonet coupling. The two lenses of the attachment replace the lens of the stereomicroscope. The attachment is provided with a quick-change mechanism, with which either the objective of the stereomicroscope or the attachment can be swung into the beam path of the stereomicroscope. This makes it possible to create an image of the front eye section through the normal objective and a wide-angle image of the fundus using the attachment. The wide-angle attachment system is adjustable for refocusing as necessary.

While the prior art system as described in U.S. Pat. No. 4,856,872 is believed to be an excellent system for wide-angle viewing of the ocular fundus, the system is also believed to have certain drawbacks. For example, the floating attachment lens requires an added secondary lens on the operating microscope to enable focal adjustment of the wide-angle lens. When the surgeon adjusts the microscope, typically using a foot-operated electrical drive system, this action moves the secondary lens and thereby requires another focusing step of the wide-angle attachment lens. Since the distance between the secondary lens and the eye determines the field of view within the eye, it is common for such adjustments to be made during surgery. With the prior art system, either the surgeon must put down his instruments and manually refocus or his assistant must refocus the wide-angle attachment with direction from the surgeon. Accordingly, it would be advantageous and is an object of the present invention to provide a system which has the capability of wide-angle viewing without the problem of refocusing of the wide-angle lens system each time the depth of field is changed.

SUMMARY OF THE INVENTION

The present invention comprises a wide-angle viewing lens attachment for use with an ocular microscope in which the attachment mounts to a support separated from the microscope. In a preferred form, the attachment includes a base member adapted for clamping attachment to a surgeon's wrist support, which support is fixed to an operating table and extends about the head of a patient on the table. A support rod extends vertically upward from the base member with a vertically adjustable carrier mounted on the support rod. A horizontally positioned ferromagnetic plate is adjustably attached to the carrier so as to extend toward the patient on the table. A lens holder including a lens clip and lens on one end of a short rod and a magnet on an opposite end of the rod allows the lens to be positioned in alignment with the patient's eye with the magnet holding the lens holder in position on the plate. Since the lens can be adjusted and focused using the attachment adjustments and is physically independent of the microscope, depth of field adjustments of the microscope do not require separate refocusing of the wide-angle attachment. The lens holder is designed to support either a contact or non-contact lens in position with the eye of a patient.

BRIEF DESCRIPTION OF THE DRAWINGS

For a better understanding of the present invention, reference may be had to the following detailed description taken in conjunction with the accompanying drawings in which:

FIG. 2 illustrates wide-angle lens attachment in accordance with the present invention for use with the microscope of FIG. 1;

FIG. 3 illustrates details of the attachment support block of FIG. 2; and

DETAILED DESCRIPTION OF THE INVENTION

Figure 1:
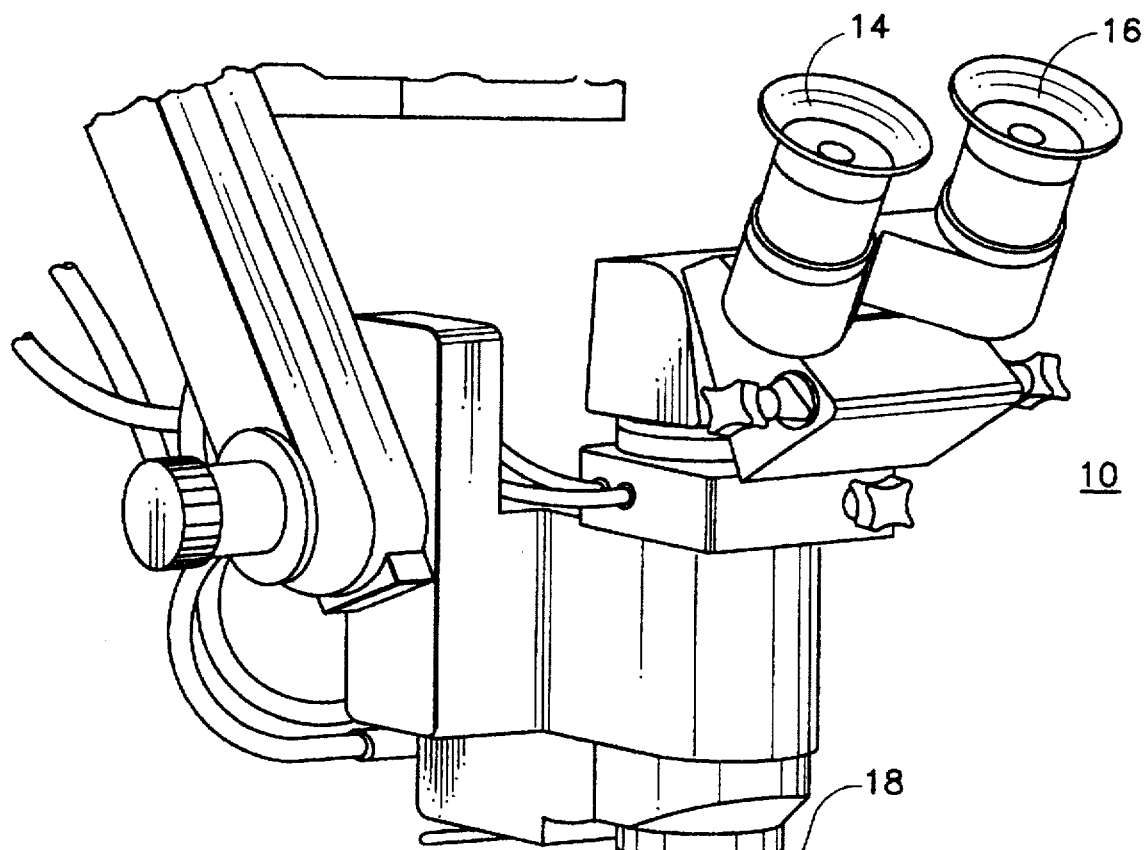
FIG. 1 illustrates a prior art microscope with lens attachment for eye surgery.

FIG. 1 illustrates a conventional binocular microscope 10 with a prior art wide-angle lens attachment 12 of the type described in U.S. Pat. No. 4,856,872 adapted for vitreoretinal surgery. The microscope 10 includes dual eyepieces 14,16 and internal prisms/lens systems (not shown) to provide magnification and focusing. An adapter 18 attaches to the lower end of the microscope, replacing the conventional objective lens, adding a reduction lens 20 and providing support for the attachment 12.

The attachment 12 is designed to support a wide-angle lens 22 at its lower end. The lens 22 fits into a spring clamp 24, which clamp extends from a vertically moveable rod 26. The rod 26 slides within a tube 28 and stays at its lowermost position due only to its weight and the weight of the lens 22. This allows the rod to be pushed vertically upward very easily so that movement of a patient undergoing eye surgery will not result in injury from the lens 22 in a contact position.

The tube 28 connects to a support member 30 which rides on a shaft 32 and a threaded element 34. A hand-nut 36 allows vertical adjustment of support member 30 for setting the lowermost position of lens 22. Both shaft 32 and element 34 are fixed to adapter 18.

In use, the surgeon selects a lens 22 and snaps or slips the lens 22 into the spring clamp 24. The microscope 10 and attachment 12 are then positioned over the patient's eye and adjusted for either contact or non-contact between the lens 22 and patient's eye. The microscope 10 is then adjusted for focus and the hand-nut 36 turned to adjust the position of lens 22 for field of view. If the microscope 10 is then repositioned for focus, the lens 22 must be readjusted. Refocusing of microscope 10 is common during surgery as the surgeon focuses on various segments of the eye. Typically, the microscope 10 includes an electronic focusing control that is foot operated so that the surgeon does not have to stop surgery for refocusing. However, with the lens attachment 12, each refocusing of microscope 10 requires a separate step of adjusting the position of lens 22.

Referring now to FIG. 2, there is shown a wide-angle viewing lens support arrangement in accordance with the present invention. In a typical surgical table for eye surgery there is provided a wrist or arm support bar extending about a patient's head positioned for use by the surgeon to rest his wrists or forearms for stabilization during surgery. A portion of such a wrist rest bar is indicated in phantom at 40 in FIG. 2. The inventive lens support arrangement includes a base block 42 having an opening 44 sized to fit about bar 40. A knob 46 is attached to a threaded rod 47 which engages a pivotable arm 48 (FIG. 3) to enable block 42 to be clamped to bar 40.

Figure 4:
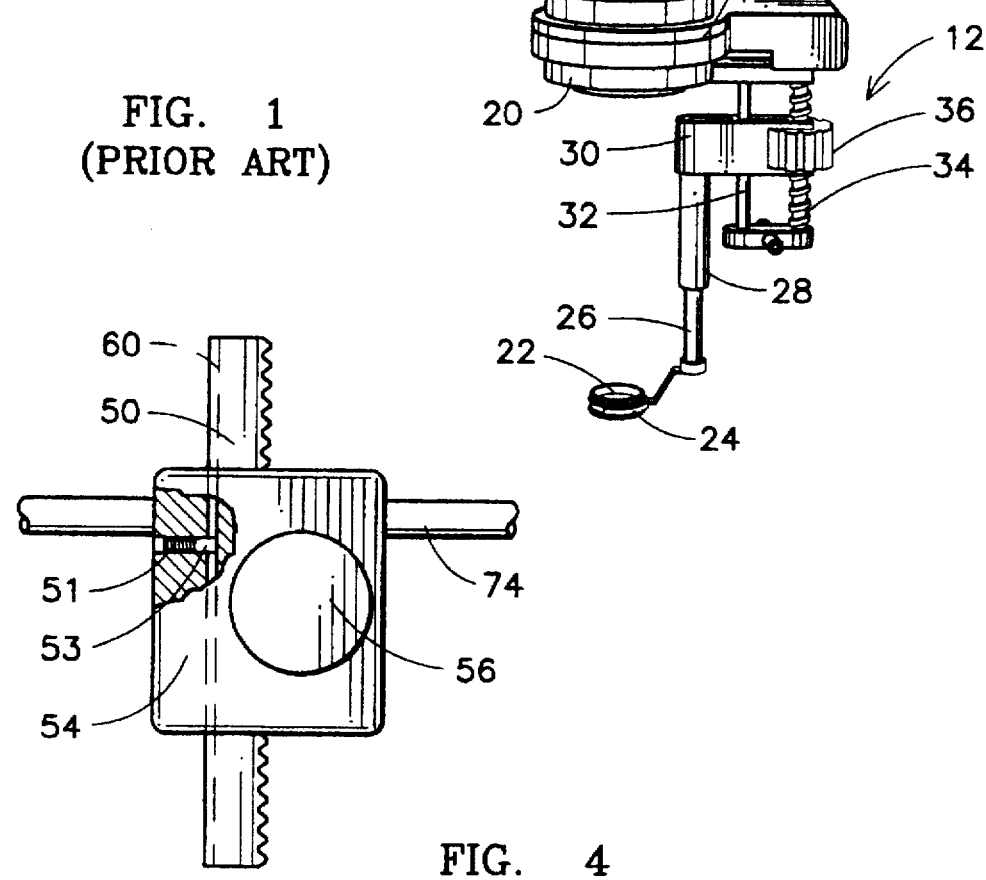
FIG. 4 illustrates details of the attachment clamp of FIG. 2.

A vertically oriented support rod 50 is affixed at one end 52 to block 42. A sliding clamp 54 fits onto rod 50 and is slidable thereon to position clamp 54 at a selected height with respect to block 42. A knob 56 attaches to a shaft 57 which drivingly engages a toothed drive gear 59 in clamp 54. While rod 50 is illustrated as generally circular, it is believed preferable to use a rod with rectangular cross-section in order to minimize any tendency of clamp 54 to rotate about the rod 50 as clamp 54 is raised or lowered. The drive gear engages a plurality of lands and grooves 58 formed over a partial circumferential extent of rod 50 and enables accurate vertical positioning of clamp 54. A vertical groove 60 extends along rod 50 and a set screw 51 (see FIG. 4) in clamp 54 drives a shaped brake insert 53 into the groove 60 to establish a pre-loading of the clamp onto the rod 50 such that the clamp remains in the vertical position established by adjusting knob 56. The brake insert 53 is preferably a synthetic material, such as Teflon, which does not bind but has sufficient coefficient of friction to prevent slippage.

The wide-angle lens shown at 62 fits into a spring clamp 64 substantially identical to clamp 24 of FIG. 1. The clamp 64 is attached to a horizontally extending rod 66 at one end and the opposite end of rod 66 is attached to a housing 68. The housing 68 contains a permanent magnet 70. The magnet 70 holds the lens assembly (lens 62, clamp 64, rod 66, housing 68 and magnet 70) in a generally stable position on a support plate 72. The plate 72 is attached to an end of a rod 74 extending through a mating aperture in clamp 54. A set screw 76 fixes the position of rod 74 in clamp 54. When properly positioned, the lens 64 will be aligned on a focal axis 78 of microscope 10. The end 75 of rod 66 connecting to clamp 64 is preferably offset to allow the lens 62 to be positioned either in eye contact or in a non-contact elevated position without the rod 66 contacting the patient's face around the eye socket. The end 75 may be welded to rod 66 as a separate element or a formed end of the rod.

In general, each element of the lens support arrangement of FIG. 2 is mechanically fixed with respect to each other element and to the operating table through the wrist rest bar 40. However, because it is not unusual for a patient undergoing eye surgery to move during surgery, the lens 62 must be capable of moving in response to such patient movement. Thus, the magnet 70 provides a releasable connection of lens 62 to the support arrangement. Further, the magnetic connection allows the surgeon to easily move the lens 62 to new positions or out of the operating field. However, the firm vertical positioning provided by clamp 54 assures that any change in focusing of the microscope 10 will not require adjustment of the position of lens 62.

While the invention has been described in what is presently considered to be a preferred embodiment, many variations and modifications will become apparent to those skilled in the art. Accordingly, it is intended that the invention not be limited to the specific illustrative embodiment but be interpreted within the full spirit and scope of the appended claims.

What is claimed is:

1. A wide-angle viewing attachment for an ocular microscope including a first lens attached to the microscope and a second lens independently mountable with respect to the microscope, said second lens being positionable proximal to an eye of a surgical patient and being maintained in the proximal position by an attachment system including a support member coupled in a fixed position to an operating table on which the patient is reclined, a first support rod extending vertically from said support member, a clamp member adjustably mounted on said support rod, a horizontally extending second support rod adjustably coupled to said clamp member, said second support rod terminating at one end in a generally flat plate, a lens carrier including a spring clamp for holding said second lens, a support arm extending generally horizontally with respect to said first support rod and terminating in a magnet assembly and said magnet assembly holding said lens carrier to said flat plate.

2. The viewing attachment of claim 1 wherein the operating table includes a wrist rest attached thereto circumscribing a patient's head position, said support member comprising a block having an opening adapted for fitting onto the wrist rest and adjustable clamping means for fixing said support member to the wrist rest.

3. The viewing attachment of claim 1 wherein said clamp member includes a drive assembly including a manual adjusting knob extending outward of said clamp member and a drive member engaging said support rod for adjusting the position of said clamp member on said support rod in response to rotation of said knob.

4. The viewing attachment of claim 3 wherein said support rod includes a plurality of uniformly spaced lands and grooves extending at least partially circumferentially about said rod and over a selected axial extent thereof, said drive member comprising a gear having teeth which mate with the lands and grooves.

5. The viewing attachment of claim 3 and including a groove formed along an axial extent of said support rod and means in said clamp member for adjustably driving an insert into said groove to minimize slipping of said clamp member on said rod.

6. The viewing attachment of claim 3 wherein an end of said lens support arm coupled to said spring clamp is bent so as to position said second lens below a longitudinal axis of said support arm.

7. The viewing attachment of claim 6 wherein said spring clamp is adapted for supporting a contact and non-contact lens.

* * * * *